United States Patent
Lancaster et al.

(10) Patent No.: US 11,141,598 B2
(45) Date of Patent: Oct. 12, 2021

(54) FAILED DIAGNOSTIC TEST ALERT OVERRIDE IN AN AUTOMATED EXTERNAL DEFIBRILLATOR (AED)

(71) Applicant: KONINKLIJKE PHILIPS N.V., Eindhoven (NL)

(72) Inventors: Gregory James Lancaster, Seattle, WA (US); Dennis E. Ochs, Woodinville, WA (US); Eric Grant Halsne, Kenmore, WA (US)

(73) Assignee: Koninklijke Philips N.V., Eindhoven (NL)

( * ) Notice: Subject to any disclaimer, the term of this patent is extended or adjusted under 35 U.S.C. 154(b) by 56 days.

(21) Appl. No.: 16/341,076

(22) PCT Filed: Sep. 27, 2017

(86) PCT No.: PCT/EP2017/074427
§ 371 (c)(1),
(2) Date: Apr. 11, 2019

(87) PCT Pub. No.: WO2018/069040
PCT Pub. Date: Apr. 19, 2018

(65) Prior Publication Data
US 2019/0232070 A1     Aug. 1, 2019

Related U.S. Application Data

(60) Provisional application No. 62/407,238, filed on Oct. 12, 2016.

(51) Int. Cl.
*A61N 1/39* (2006.01)
*G08B 3/10* (2006.01)
*H04B 1/3827* (2015.01)

(52) U.S. Cl.
CPC ......... *A61N 1/3931* (2013.01); *A61N 1/3904* (2017.08); *A61N 1/3993* (2013.01); *G08B 3/10* (2013.01); *H04B 1/3827* (2013.01)

(58) Field of Classification Search
CPC .. A61N 1/3931; A61N 1/3904; A61N 1/3993; G08B 3/10; H04B 1/3827
See application file for complete search history.

(56) References Cited

U.S. PATENT DOCUMENTS 5,073,085 A    12/1991  Ito et al.
5,879,374 A *   3/1999  Powers ............... A61N 1/3925
                                                 607/5

(Continued)

FOREIGN PATENT DOCUMENTS

EP     1419798 A2     5/2004
WO  2009147678 A2    12/2009

OTHER PUBLICATIONS

PCT/EP/2017/074427, ISR and Written Opinion, dated Dec. 13, 2017.

*Primary Examiner* — Carl H Layno
*Assistant Examiner* — Manolis Pahakis

(57) ABSTRACT

A defibrillator such as an automated external defibrillator (AED) includes a manual override feature which enables the AED to reduce the power consumption and owner annoyance after a self-testing fault. The AED, upon sensing a press of a manual override button or a receipt of an acknowledgement signal from a remote service provider, defers one or both of an alarm output and a subsequent self-test for a predetermined correction period. The deferral allows the user to correct the self-test fault during the correction period without further annoyance.

16 Claims, 6 Drawing Sheets

(56) References Cited

U.S. PATENT DOCUMENTS

| | | | | |
|---|---|---|---|---|
| 6,073,085 A * | 6/2000 | Wiley | G06F 11/22 | 702/118 |
| 6,148,233 A * | 11/2000 | Owen | A61N 1/3925 | 607/5 |
| 6,725,074 B1 * | 4/2004 | Kastle | A61B 5/14551 | 600/323 |
| 7,594,125 B2 * | 9/2009 | Zhong | H04W 52/0216 | 713/300 |
| 10,610,160 B1 * | 4/2020 | McNair | G08B 21/0453 | |
| 2011/0060378 A1 * | 3/2011 | Tuysserkani | A61B 5/0022 | 607/5 |
| 2012/0016215 A1 * | 1/2012 | Condurso | A61B 5/021 | 600/316 |
| 2012/0081230 A1 * | 4/2012 | Sullivan | G08B 3/10 | 340/636.1 |
| 2012/0150247 A1 * | 6/2012 | Meier | H01M 10/425 | 607/5 |
| 2015/0070187 A1 * | 3/2015 | Wiesner | A61B 5/0022 | 340/870.02 |
| 2015/0099458 A1 * | 4/2015 | Weisner | G06F 19/3418 | 455/15 |
| 2015/0118658 A1 * | 4/2015 | Mayou | A61B 5/165 | 434/127 |
| 2015/0148857 A1 * | 5/2015 | Macho | A61N 1/3993 | 607/7 |
| 2015/0254956 A1 * | 9/2015 | Shen | A61B 5/1117 | 340/573.1 |
| 2015/0265844 A1 | 9/2015 | Powers et al. | | |
| 2016/0274162 A1 | 9/2016 | Freeman et al. | | |
| 2017/0027527 A1 * | 2/2017 | Bhat | A61B 5/7275 | |
| 2017/0095217 A1 * | 4/2017 | Hubert | G16H 40/67 | |
| 2017/0095674 A1 * | 4/2017 | Hresko | A61N 1/3937 | |
| 2017/0164832 A1 * | 6/2017 | Kaib | G16H 40/63 | |
| 2017/0296810 A1 * | 10/2017 | Thakur | A61N 1/37 | |
| 2018/0113498 A1 * | 4/2018 | Cronin | A61B 5/6804 | |

\* cited by examiner

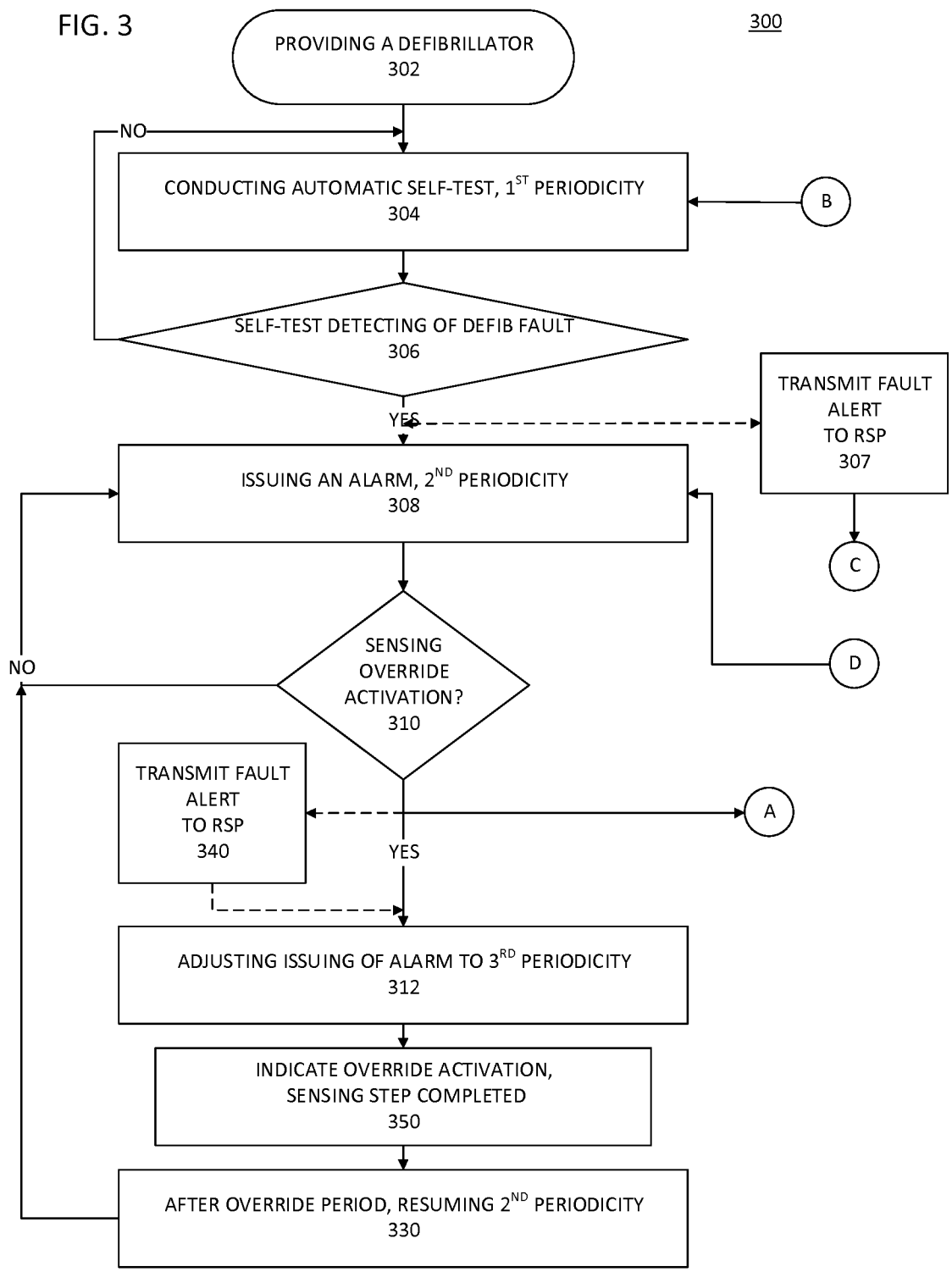

| STATE NO. | ALERT STATE | ALERT CONDITION | ALERT TYPE | OVERRIDE ACTION | OVERRIDE PERIOD |
|---|---|---|---|---|---|
| 0001 | LOW BATTERY | <25% REMAINING | VISUAL / AUDIBLE | TURN OFF AUDIBLE, REDUCE SELF-TEST FROM DAILY TO WEEKLY | 1 MONTH |
| 0002 | CRITICAL BATTERY | <5% REMAINING | VISUAL / AUDIBLE | TURN OFF AUDIBLE, REDUCE SELF-TEST FROM DAILY TO WEEKLY | 5 DAYS |
| 0003 | ELECTRODE INTEGRITY | GEL IMPEDANCE OUT OF RANGE | VISUAL / AUDIBLE | REDUCE AUDIBLE | 5 DAYS |
| 0004 | CIRCUIT FAULT | COMPONENT FAILURE DETECT | VISUAL / AUDIBLE | REDUCE AUDIBLE | 2 DAYS |
| 0005 | PERIODIC MAINTENANCE | ELECTRODES ETC BEYOND SHELF LIFE | VISUAL | TURN OFF AUDIBLE | 1 MONTH |

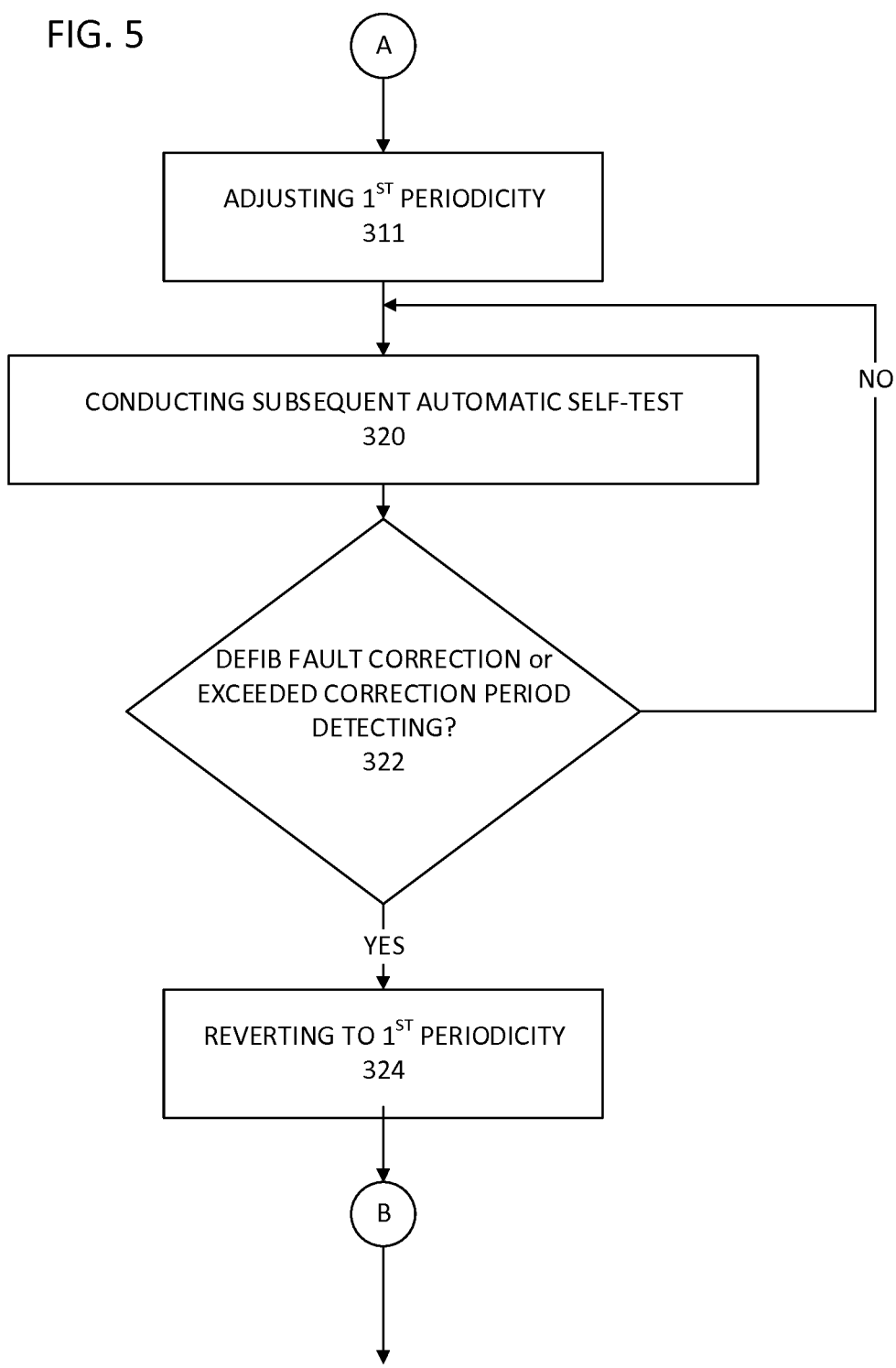

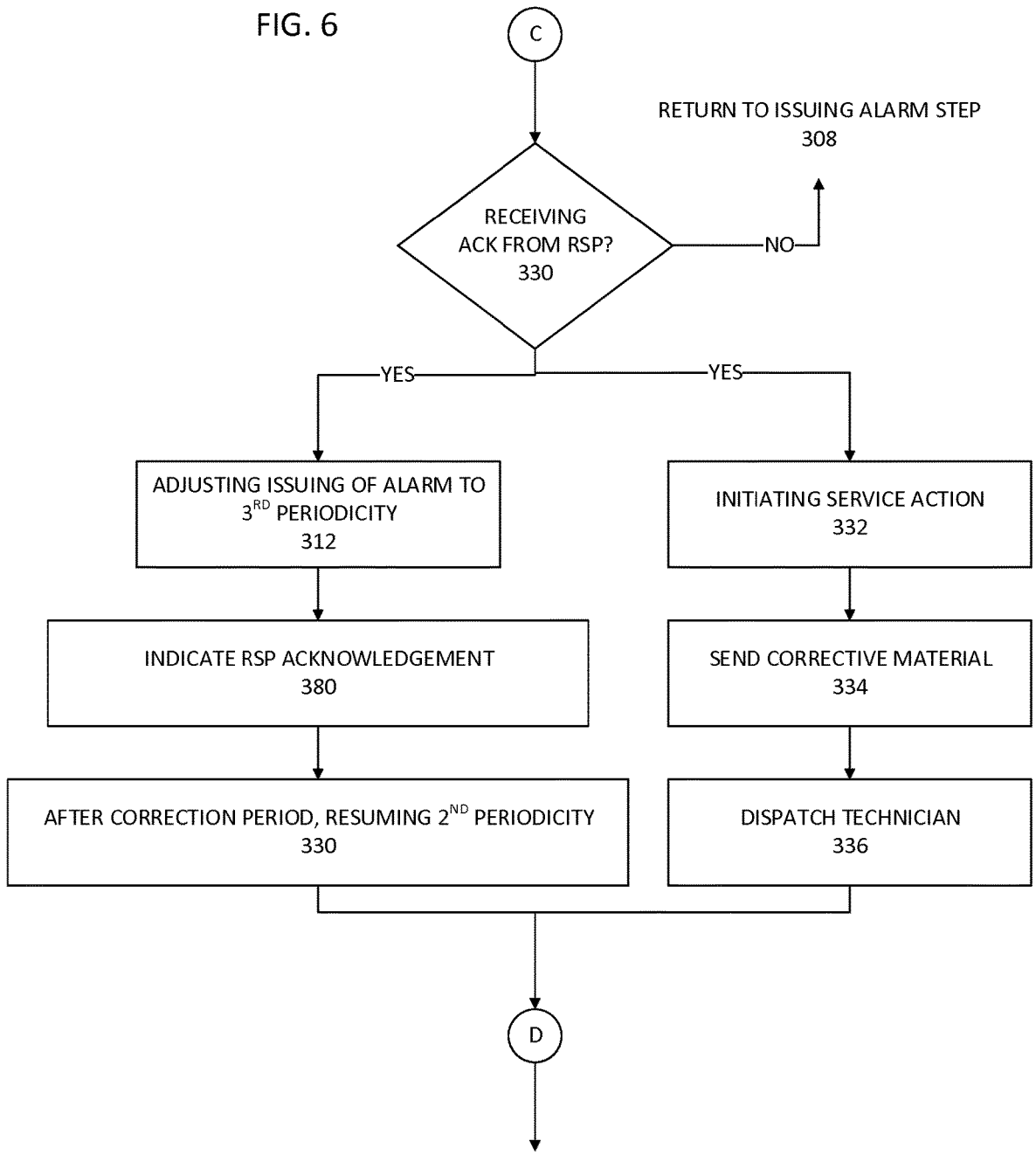

FAILED DIAGNOSTIC TEST ALERT OVERRIDE IN AN AUTOMATED EXTERNAL DEFIBRILLATOR (AED)

CROSS-REFERENCE TO PRIOR APPLICATIONS

This application is the U.S. National Phase application under 35 U.S.C. § 371 of International Application No. PCT/EP2017/074427, filed on Sep. 27, 2017, which claims the benefit of U.S. Provisional Patent Application No. 62/407,238, filed on Oct. 12, 2016. These applications are hereby incorporated by reference herein.

BACKGROUND OF THE INVENTION

Cardiac arrest, ventricular fibrillation and cardiac arrhythmia are life-threatening heart conditions that require immediate cardiopulmonary resuscitation (CPR) and defibrillation to increase one's chances of survival. Defibrillation is a treatment that involves the delivery of an electric shock that allows reestablishment of the normal contraction rhythms of the heart.

Automated external defibrillators (AEDs) are easy-to-use, accessible, portable devices that are used to deliver defibrillation treatments. AEDs are usually deployed for long periods in public spaces, such as in schools, parks, residential areas, ambulances, and even police vehicles, in order to immediately respond to cardiac emergencies occurring in a public place. It is thus essential that deployed AEDs are always functional and ready for use in case of such emergencies.

Most AEDs are equipped with self-diagnosing, or self-testing, functions in order to periodically and automatically determine the usability of the AED while in deployment. Typically, alarms are generated based on the results of the self-tests to notify the appropriate party regarding, for example, the need for AED maintenance or repair.

WO 2009/147678 discloses a pocket defibrillator capable of performing self-tests to determine proper operation of the pocket defibrillating system. Alerts are displayed when equipment malfunction is determined based on the performed self-test results.

U.S. Pat. No. 5,879,374 discloses an AED that performs periodic self-tests to verify that the AED's components and operation are within preset specifications. A visual alert and an alert buzzer are activated to indicate non-readiness of the AED for use when the system does not receive proper test confirmation. U.S. Pat. No. 5,879,374 is incorporated herein by reference.

The inventors have discovered that there are times when a user's response to self-testing failure or fault alert, indicating that the AED is not completely ready for use, is improper. Reasons for this may include that the AED is stowed in an inaccessible place, the user is too busy to respond, or a responsible user is not available to take care of the AED. The self-test alert in prior art AEDs will usually recur until the battery is completely drained. Such a completely inoperable AED may thereafter be left in place long after the alerts have ceased.

Battery life is also significantly reduced by the recurring fault alerts and/or repeated self-tests that determine the same fault cause. Thus, an AED that is alerting a self-test fault, but may still be operable to deliver a defibrillating shock in some fashion, may drain its battery prematurely and unnecessarily.

In addition, some users simply remove the AED battery when it begins to alert to a failed self-test, with the intention to someday correct the fault, or to save battery life in order to use the AED when needed. But removal of the battery increases the time to respond to a sudden cardiac arrest substantially, because reinsertion of the battery generally initiates some self-testing or the battery may be difficult to locate. And user inattention to the fault state that is quieted by battery removal may result in no corrective action being taken at all.

In light of these discovered problems with the user interaction with defibrillators needing maintenance attention, then, what is needed is an improved method for responding to an AED self-testing fault or failure alert. Such an improved method would enable the user to correct the failure without undue inconvenience, and more expeditiously than prior art methods.

BRIEF SUMMARY OF THE INVENTION

The present invention relates to methods and associated apparatus's for activating and deactivating self-testing alerts on external defibrillators, such as automated external defibrillator (AED). The inventive apparatus is an AED having a self-test alerting manual override button. A sensed press of the override button may initiate a number of device responses that reduce alarm annoyance, simplify local corrective action, save battery power, and automatically alert remote service providers to assist in the corrective actions. Exemplary device responses to a sensed override button press may be a temporary reduced frequency of automatic self-tests, a reduced frequency of alarm activations, automatic notification of a remote service provider via a communications circuit, and/or local indications that the default self-testing protocol has been modified by the override button.

Accordingly, one preferred embodiment of the inventive apparatus is a defibrillator comprising a housing, a self-test circuit disposed within the housing and being configured to conduct an automatic self-test of the defibrillator on a first periodicity and being further configured to provide an initial determination output of a result of the self-test, and a manual self-test override input disposed on an exterior surface of the housing. The defibrillator further comprises an audible output in communication with the self-test circuit, the audible output operable to activate in response to the determination output, and a hardware processor in communication with the manual self-test override input and the self-test circuit, wherein the hardware processor is configured to adjust the determination output in response to a sensed operation of the manual self-test override input.

The defibrillator may further be configured to adjust the determination output by one of a deferral of the initial determination output and a reduction in a frequency of the initial determination output for a predetermined correction period. The defibrillator hardware processor may further be configured to revert to the initial determination output at the end of the predetermined correction period.

The defibrillator may further comprise a wireless transceiver controllably coupled to the hardware processor, wherein the hardware processor and transceiver are configured to transmit a self-test fault alert responsive to one or both of the sensed operation of the manual self-test override input or to the initial determination output of a failed self-test.

According to another embodiment, a method is described for maintaining a defibrillator, comprising the steps of providing a defibrillator apparatus as described previously, conducting an automatic self-test, detecting a self-test fault, and issuing an alarm via the audible output responsive to the detecting step, the alarm repeating at a second periodicity. The method continues with the step of sensing an activation of the manual self-test override input subsequent to the issuing step, adjusting the issuing of the alarm to a third periodicity based on the sensing step, and resuming the issuing of the alarm at the second periodicity after a predetermined correction period.

The method may further include steps of adjusting the first periodicity based on the sensing step, conducting a second automatic self-test subsequent to the adjusting step, detecting a correction of the self-test fault, and reverting to the first periodicity that was in effect prior to the sensing step.

The method may further include steps of transmitting a self-test fault alert via the wireless transceiver to a remote service provider responsive to the detecting step or the sensing step, and receiving at the wireless transceiver an acknowledgement subsequent to the transmitting step. The adjusting step and the resuming step may be further based on the receiving step. In other embodiments, a remote service provider initiates a service action based on a receiving of the self-test fault alert, and/or the service action comprises sending corrective material to the location of the defibrillator, and/or the service action comprises dispatching a technician to the location of the defibrillator.

The preferred embodiments of the invention allow for a manual override button (such as an information i-button) that is located on the AED housing to be pressed to delay further alerting, or to defer self-testing for a predetermined correction period. Such a feature allows for time to correct the fault without unnecessary continual alerting, and also results in a longer battery life because of more infrequent activations of the visual and audible indicators. Such a feature is particularly advantageous if the fault is a non-fatal fault, such as "low battery", which indicates that the AED may be used if needed during an emergency even in the presence of the fault. A press of the override button may result in a correction period of for example five days before reverting to the default self-test alerting sequence of every several seconds. This provides additional time for the user to obtain new parts or to otherwise correct the fault.

In situations in which the self-test fault is a fatal fault, i.e. the AED is completely inoperable for emergency use, then a preferred embodiment is one in which the override, by button or by a wireless communications link to a remote service provider, may be enabled for just a short time, such as about 24 hours. Only if an acknowledgement from the remote service provider is received at the AED will an override period be automatically extended.

In other embodiments of the invention, both fatal and non-fatal self-test faults may not be overridden until a confirming acknowledgement of the fault is received from the remote service provider. In other embodiments, a press of the i-button on the AED if a self-test fault exists may cause the AED to issue a voice guidance message, such as "Not ready for use. Contact the service provider at the telephone number on the back of this device to override this alert."

BRIEF DESCRIPTION OF THE DRAWINGS

The accompanying drawings, which are included to provide a further understanding of the invention, are incorporated herein to illustrate embodiments of the invention. Along with the description, they also serve to explain the principle of the invention. In the drawings:

FIG. 3 is a flowchart describing the method of adjusting self-testing alerts based on diagnostic test results in a defibrillator.

FIG. 4 illustrates an embodiment of an alert state database as stored in the defibrillator or AED memory.

FIG. 5 is a flowchart describing additional embodiments of the method of adjusting self-testing alerts in a defibrillator.

FIG. 6 is a flowchart describing additional embodiments of the method of adjusting self-testing alerts in a defibrillator.

DETAILED DESCRIPTION OF THE VARIOUS EMBODIMENTS OF THE INVENTION

Figure 1:
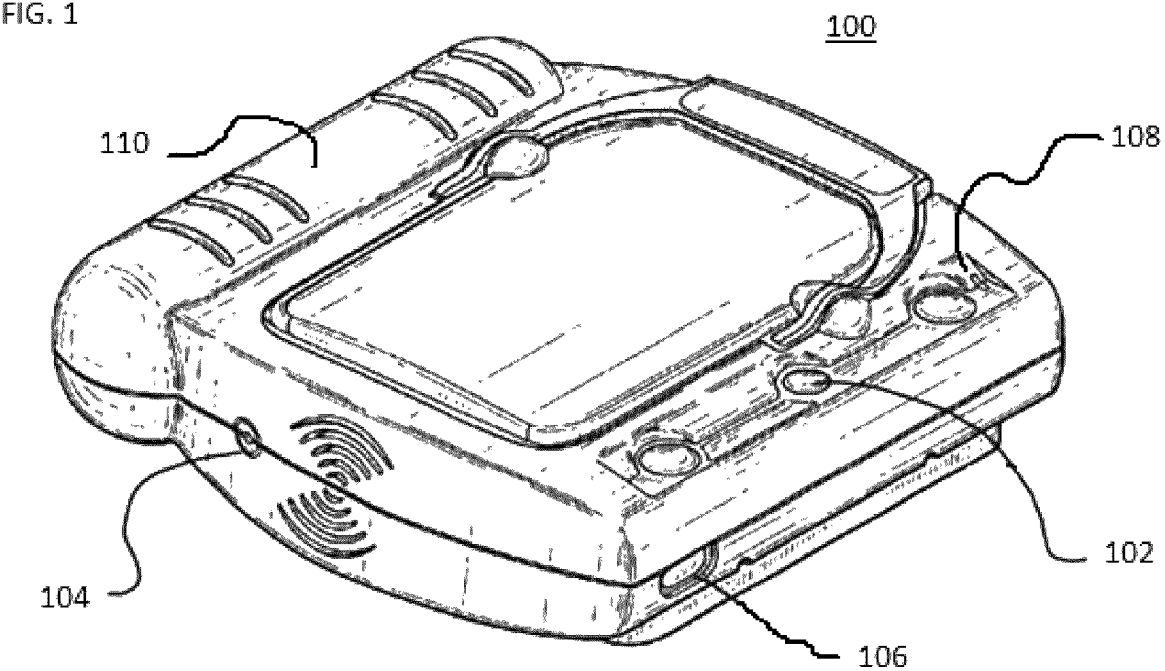
FIG. 1 illustrates a defibrillator such as an AED, having manual override controls for quieting self-testing alerts, according to one embodiment of the present invention.

The following are definitions of terms as used in the various embodiments of the present invention.

The term "self-test" or "diagnostic test" as used herein refers to the AED's automated self-diagnostic function for determining the operability state of the AED based on the condition of its components. The diagnostic test includes, but is not limited to, a battery test for determining the remaining power available to the AED, a CPU state test for determining if the AED's internal registry and memory are accessible, a memory space test for determining the AED's free memory, an electrodes integrity test for determining usability of electrodes based on electrode expiration date or a sensed condition of the electro-gel, an ECG calibration test for ensuring ECG monitoring function of the AED is accurate, or a sensed expiration of shelf life for device or accessories.

The term "operability state" as used herein refers to the AED's usability condition determined by a diagnostic test performed at a specific time. The AED operability state relates to all the parameters tested and determined by the diagnostic test. These parameters may include battery level, CPU state, memory space status, electrodes integrity, ECG calibration status, among others. The AED's operability state includes a standard operable state and an alert state, wherein the alert state is determined by matching the determined operability state with stored alert states in the AED memory.

The term "alert" as used herein refers to any action the system may execute in response to a determined operability state of the AED to call immediate attention towards the AED for device maintenance and repair. Examples of alerts are prompting visual indicators, audio alarms, and vibratory alarms, sending messages alerting service personnel and community administration, or any combination thereof, among others.

The term "database" as used herein refers to a collection of data and information organized in such a way as to allow the data and information to be stored, retrieved, updated, and manipulated and to allow them to be presented into one or more formats such as in table form or to be grouped into text, numbers, images, and audio data. The database typically resides in computer memory that includes various types of volatile and non-volatile computer memory. "Database" as used herein also refers to conventional databases that may reside locally or that may be accessed from a remote location, e.g., remote network servers. The term "database" as used herein may also refer to a segment or portion of a larger database, which in this case forms a type of database within a database. Memory wherein the database resides may include high-speed random access memory or non-volatile memory such as magnetic disk storage devices, optical storage devices, and flash memory. Memory where the database resides may also comprise one or more software for processing and organizing data received by and stored into the database.

Terms referring to electrical components such as processors, clocks, memory, modules, inputs, outputs, display, systems, transceivers, power sources, and the like are understood to be circuit hardware as commonly understood in the art. Such circuit components may be integrated together in whole or in part such as in ASICS, hardware microprocessors, Field Programmable Gate Arrays (FPGA), random access memory, fixed memory modules, and the like. The system comprising the circuit components may be under the control of software instructions that reside in memory and are executed by various computing hardware in the AED.

Now turning to the FIGURES, FIG. 1 illustrates the external portion of a defibrillator or AED 100 according to the present invention. The invention relates to a system for activating and deactivating a self-testing alert in the AED, comprising a diagnosing system for determining an operability state of the AED, an alert system for activating an at least one alert based on the determined operability state, an override system for deactivating for a predetermined period the at least one generated alert, a communication system for sending the at least one alert to a remote device, and a processor for controlling the diagnosing system, the alert system, the override system, and the communication system.

FIG. 1 illustrates the exterior features of an automated external defibrillator (AED) 100 system with an alert override system according to a preferred embodiment of the present invention. AED 100 includes a housing 110, inside of which are circuits including a hardware processor or controller 126 and clock 122 configured to control an AED self-testing circuit 120. As will be described in more detail, hardware processor 126 periodically activates the self-testing circuit 120 during low-power standby conditions to conduct a diagnostic self-test. The self-test result is conveyed via an initial determination output to the user or a remote service provider (RSP). The result is also stored in a memory 116/117. The hardware processor 126 then returns the device to standby to conserve power.

AED 100 conveys a self-test result to the user via one or more of a defibrillator display 112 (not shown in FIG. 1), a self-test status audible output 104 such as a buzzer or beeper, and a self-test status visual output 108 such as an LED or LCD indicator light, all of which are disposed in communication with the self-test circuit 120. The outputs are preferably arranged on the housing 110 such that a user can easily hear or see indications relating to the result.

In communication with hardware processor 126 is a manual self-test override input 102, which may be co-located with an AED informational button (i-button) or may alternatively be a stand-alone override button. The override input is disposed on the exterior surface of housing 110. Optionally in controllable communication with hardware processor 126 is a bi-directional and wireless communications transceiver 106. Wireless transceiver 106 is configured to transmit a self-test fault alert responsive to a sensed operation of override input 102 or responsive to a detected self-test fault. The transmission is directed to an external (remote) communicator device 124 and/or a remote service provider control station 160.

Figure 2:
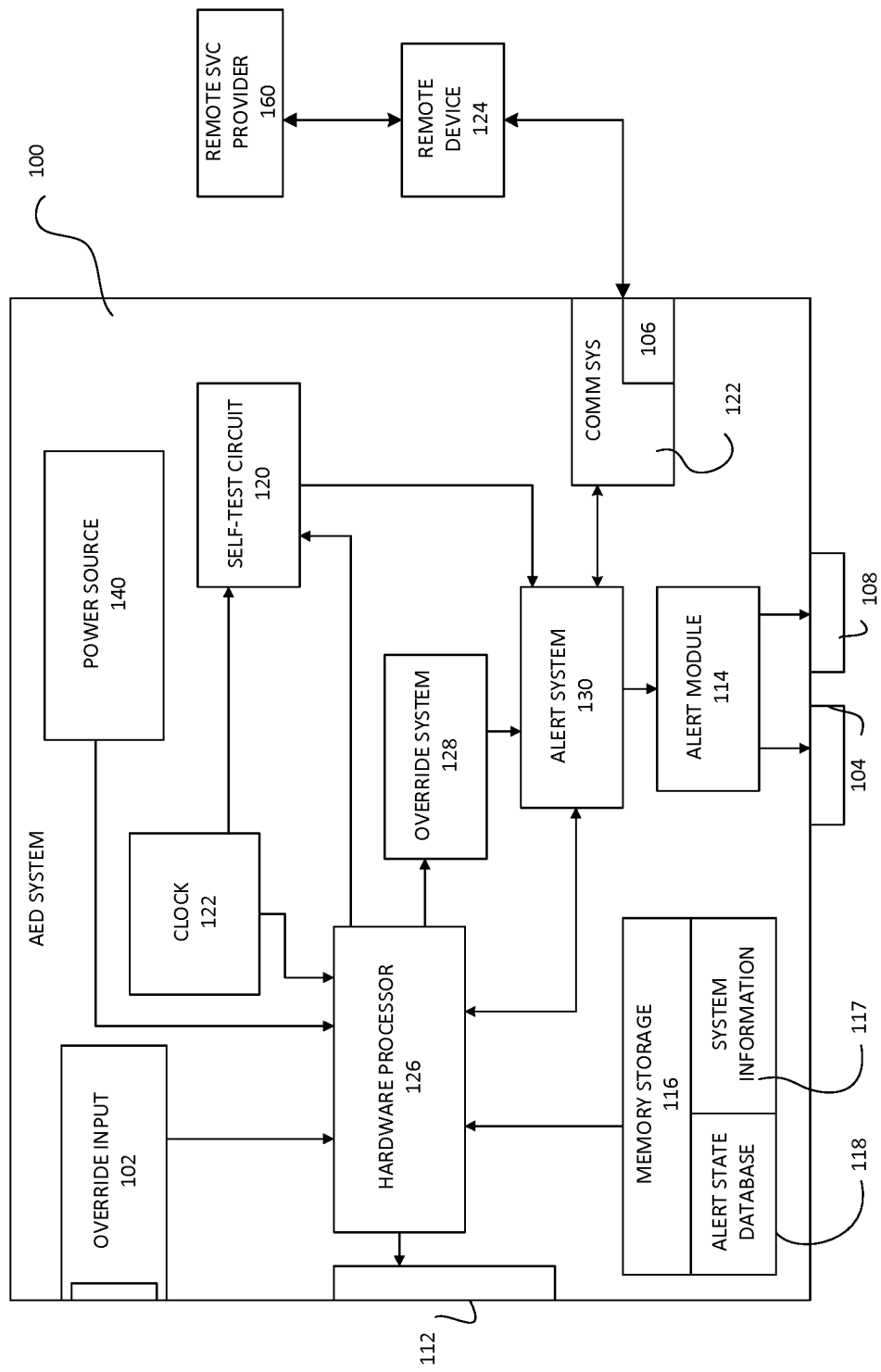
FIG. 2 illustrates a system electrical schematic diagram of a defibrillator having manual override controls for quieting self-testing alerts, according to a preferred embodiment of the present invention.

The schematic diagram of FIG. 2 illustrates the internal components of a preferred AED 100. The central control of AED 100 functions may be conducted by hardware processor 126, which senses a user press of the manual override input 102 and otherwise operates under control of clock 122. Software instructions for processor 126 may be stored in memory 116. Power for the system may be provided by power source 140 that may be a rechargeable or primary battery.

Clock 122 and processor 126 also control the activation and conduct of self-test circuit 120. When not in use, AED 100 is in a low-power standby mode of operation, wherein the self-test circuit 120 periodically activates and tests various components of the device on a schedule. Low-voltage and battery components may be tested on a daily schedule. High-voltage defibrillation components may be tested on a bi-weekly or monthly schedule. Results (determinations) of the tests are conveyed via an alert system 130 and alert module 114 to visual and audible outputs 104/108. Successful results are preferably indicated by silence and a ready for use indicator light: Unsuccessful results may be indicated by a beep and a rapidly flashing light. Optionally, test results may be displayed in text or graphic format at display 112.

An operation of override input 102 causes hardware processor 126 to adjust the above-described self-testing schedule and/or the alerting outputs via optional override system 128 and alert system 130. For example, hardware processor 126 may cause further determination outputs to be deferred, or their frequency reduced, or the nature of the outputs, for a predetermined correction period to allow the user to correct a detected fault. Alternatively, processor 126 may be configured to reduce the frequency of the automatic self-test to a second periodicity in response to the override input. Alternatively, processor 126 may be configured to modify the self-test responsive to the override input. The modification may be for example temporary suspension of higher-power self-testing operations, such as high-voltage tests, in the case of a low battery self-test fault. These features reduce the annoyance of ongoing alarms and preserve battery life while corrective action is underway. Alternatively, the afore-described override functionality may be off-loaded from processor 126 to a separate override system 128 processor.

FIG. 2 illustrates wireless transceiver 106 as a component of a communication system 122 that is in communication with processor 126 and alert system 130. Transceiver 106 is preferably bi-directional and may be of wireless (WiFi), telephonic, wired, or infrared (IR) function and the like. Transceiver 106 is configured to transmit a self-test failure alert responsive to either of a sensed operation of the override input 102 or to an initial determination output of a failed self-test. The transmission is preferably directed to remote device 124 and/or a remote service provider control station 160. Transceiver 106 is preferably configured to receive an acknowledgement of the transmission from the remote device/system, whereupon the processor 126 may further defer self-tests or reduce self-testing periodicity and outputs because RSP corrective action is underway. Acknowledgement may also cause processor 126 to indicate that corrective action in ongoing by third parties at display 112 or the like. FIG. 2 shows remote device 124 optionally as a relay between AED 100 transceiver 106 and remote service provider 160. In this embodiment remote device 124 may be configured to covert for example a received infrared signal from transceiver 106 to a wireless RF signal for further transmission to RSP 160.

In all cases described above, AED 100 preferably reverts the frequency and nature of self-test fault outputs to their initial settings (e.g. the first periodicity of self-testing schedule) after a predetermined correction period has lapsed. This reversion ensures that an override action never places AED 100 into a permanent corrective action deferral state.

AED 100 may respond to a sensed press of manual override input 102 in yet other ways. For example, if the override button is pressed when AED 100 is in a "ready for use" state, AED 100 may issue an audible prompt from its speaker that "the AED is ready for use. To defer the next xx self-tests, press the override button again." The term "xx" indicates a predetermined number of self-tests, as configured by a device manufacturer or administrator. If AED 100 then senses an additional override button press, AED 100 then defers the predetermined xx number of self-tests to save battery life.

In another example, a sensed press of the input 102, e.g. a manual override button, when AED 100 has a fault condition may cause processor 126 to issue an audible prompt that "the AED is not ready for use. Contact the manufacturer at the telephone/internet number on the back of the device to override this alert." Optionally, a brief fault override may be initiated. The manufacturer can then remotely override further fault indications via the transceiver 106 for a longer corrective action period in order to reduce alarm annoyance and battery drain.

FIG. 3 is a flowchart describing one method 300 for maintaining a defibrillator. In particular, the method is to the adjusting of self-testing functionality based on a sensed user interaction responsive to self-test diagnostic test results or determinations. The method addresses the problems of users responding to a self-test fault alert, i.e. audible and/or visual alarms which may become annoying after persisting for a long duration, by providing a device by which the user can appropriately override the alarm for a predetermined time to allow for corrective action, and which offers an alternative to detrimental removal of a battery for "quieting" of alarms.

Method 300 begins by a providing step 302 of a device such as a defibrillator that has an automatic self-testing circuit which provides a periodic self-test of components while the device is not in use. The apparatus is generally configured as previously described. The defibrillator departs from prior art devices by including a manually operated self-test override input 102 and a hardware processor 126 which is configured to adjust a self-test determination output based upon a sensed operation of the override input. Method 300 is preferably administered by execution of software instructions by processor 126 and/or associated device circuitry.

After being placed into operation in a standby condition (i.e. not in use for a cardiac rescue), the defibrillator automatically conducts a self-test upon a predetermined schedule at conducting step 304. Exemplary schedules are daily, weekly, and monthly tests, although the exact nature and schedule of tests may vary within the scope of the invention. The self-test is triggered by on-board clock 122 and is preferably controlled by software instructions executed by hardware processor 126 and self-test circuit 120.

Conducting step 304 is of course for the purpose of detecting a fault in AED 100 circuitry. Method 300 thus includes a decision block step of detecting a self-test fault 306, of either a "ready for use" condition or a fault condition.

A common result of the self-test is a determination of "ready for use", i.e. no fault is determined. AED 100 then powers down and returns to the low-power standby condition. AED 100 provides some sort of indication that the device is ready for use. An exemplary ready condition is a flashing "ready" light with no audio output. A sensed press of an i-button in this state may initiate an audible or displayed status message such as "ready for use."

Part of method 300, but not shown in FIG. 3, may include a step of responding to a sensed press of manual override input 102 when AED 100 is in a "ready for use" state between steps 302 and 304. In this state, a sensed input initiates a step of issuing an audible prompt from the AED 100 speaker that "the AED is ready for use. To defer the next xx self-tests, press the override button again." The term "xx" indicates a predetermined number of self-tests, as configured by a device manufacturer or administrator. If an additional override button press is then sensed by the method, AED 100 then defers the predetermined xx number of self-tests to save battery life. If no such override button press is sensed for a predetermined time, then the AED 100 returns to the standby state just prior to step 304 and continues method 300 according to the self-test schedule.

If defibrillator/AED 100 detects one or more device faults during the detecting automatic self-test step 306, then method 300 proceeds to an issuing an alarm step 308. Alarm step 308 is initially according to the "default" alarming protocol for the device. For example, an audible annunciator may provide a loud chirp or series of chirps during a fault condition that alerts anyone in the vicinity that the AED 100 is not fully operable. Some faults, such as a low battery, may not render the device fully inoperable. In such cases a single chirp may be issued on a second periodicity such as every 6 seconds. Other faults, such as a defibrillating circuit failure may be fatal, and so a triple chirp may thus be issued from output 104 along with a flashing light from visual output 108. Information about the fault may be displayed on display 112. The visual and audible alarms preferably continue at the second periodicity until the fault is corrected or all of the battery power is consumed.

The AED 100 alarms may bring the fault to the attention of the owner or administrator of the device. Typically, corrective action begins at that time. But there is a delay between alarming and corrective action during which the alarm continues. Sometimes a nearby user may merely remove the battery from the device in order to silence an ongoing and annoying alarm. This situation is sub-optimal because if the AED 100 is needed for a cardiac rescue, there is uncertainty as to whether the device is operable (i.e. no status indications are available). Re-insertion of the battery also entails time-consuming initiation tests during the rescue, which delays defibrillating treatment. Such delays can be fatal to the victim of sudden cardiac arrest.

The present invention solves the aforementioned problem by providing a manual self-test override input 102 with AED 100, and by providing a step 310 of sensing an activation of the manual self-test override input subsequent to the issuing step 308. The sensing may be in response to a manual override button press on the device itself, for example. The sensing may also be in response to a wireless acknowledgment signal input from a remote service provider which is itself initiating corrective action.

The AED 100 method 300 may provide an optional indicating step 350 for indicating that the override activation at step 310 has occurred. This may be a graphic or textual display on display 112 or may be a dedicated alarm indicator light. The indicator may also comprise an audible prompt such as "self-test override has been activated" that issues in response to a button press.

Method 300 responds to a sensing of the override activation from sensing step 310 with an adjusting step 312. Adjusting step 312 is an adjusting of the self-test alarm to a third and more infrequent periodicity based on sensing step 310. For example, adjusting step 312 may reduce a fault chirp to once an hour instead once every few seconds. In addition, adjusting step 312 may cause the fault chirp to issue at a much lower volume in order to reduce annoyances. Adjusting step 312 periodicity may also be reduced to zero, silencing the alerts altogether.

The reduced periodicity of adjusting step 312 is intended to be temporary, and should be no longer than is reasonably necessary to correct the underlying fault. The duration of the reduced periodicity is predetermined and preset in the device behavior by the manufacturer or the administrator of the device. This duration is called the override period or pre-determined correction period. FIG. 4 provides some examples of the override periods.

After the predetermined correction period has elapsed, method 300 continues with a step 330 of resuming of the self-test alarm at the second periodicity. Step 330 thus ensures that a testing override does not become inadvertently permanent. Step 330 also ensures that alarms resume at their initial periodicity regardless of whether corrective action has occurred or not. After the second periodicity of alarming resumes at step 330, method 300 proceeds back to the initial issuing of alarms at step 308. Of course, the override activation steps 310, 312, 350 etc. may thereafter be repeated as necessary.

Method 300 may also include an adjusting of the first periodicity step 311, i.e. the periodicity of further self-tests, responsive to sensing step 310. FIG. 5 illustrates this optional branch "A" of the method. Step 311 may serve in particular to extend battery life by reducing the power consumption related to conducting self-tests. For example, a low battery fault or a critical battery fault indicates impending battery exhaustion. For low battery alarms (without other faults detected) it may be desirable to adjust self-testing frequency from a daily basis to a weekly or even monthly basis in step 311. Low battery alarms without further faults may further cause step 311 to reduce high-voltage self-tests from monthly to semi-monthly for example.

The self-test adjusting branch A of method 300 continues at a step 320 of conducting one or more automatic self-tests at the adjusted first periodicity. The adjusted first periodicity may be zero for that particular self-test. Alternatively, the adjusted first periodicity may be a reduction of the self-test frequency from daily to weekly, from weekly to semi-weekly or monthly, or from monthly to semi-monthly. FIG. 4 illustrates some exemplary options in the "Override Action" column.

A detecting self-test fault correction step 322 occurs at the end of conducting step 320. Included in step 322 is a detecting of whether a correction period for the first periodicity has elapsed. This correction period is preferably the same as the override period described previously, but may optionally be different. The self-test fault correction may be automatically sensed by an automatic self-test, by a user input, or by a wireless notification from a remote service provider for example. If AED 100 detects either of a corrected fault or an elapsed correction period (the YES branch in FIG. 5), then the method 300 proceeds by reverting to the default or initial first periodicity of self-testing scheduling that was in effect prior to the sensing step and returning to the device standby mode of operation at conducting step 304. Otherwise, method 300 proceeds back to step 320 to operate at the adjusted first periodicity. The return in shown by reference "B" in FIGS. 3 and 5.

FIG. 4 illustrates an exemplary alert state database 118 which may be stored in memory 116. Database 118 contains the parameters for adjusting the device operation in response to a sensed override button press. It is understood that database 118 parameters are predetermined and may be pre-adjusted by the manufacturer or a device administrator before AED 100 is placed into operation. The parameters may be modified via a software program residing on AED 100, via a remote service provider software that is in communication with AED 100, or with a local computer communicating with AED 100.

FIG. 4 illustrates that the AED 100 and method 300 response to a self-test override signal may differ depending on the type of self-test fault. For example, override of a low or critical battery fault condition may entail turning off audible alarms for differing override periods. A low battery condition may allow for a longer correction period, e.g. one month, than a critically low battery condition, e.g. five days. Similarly, electrode integrity may be sufficient for a successful use for a period after the gel impedance is found out of range. An override period of five days or longer may be sufficient for an electrode fault. But a circuit fault may be "fatal", and so the shortest override period, e.g. two days, may be appropriate. And perhaps in this case no override period may be permitted at all. Finally, if simply a shelf life or maintenance period is exceeded (detected by clock 122 or equivalent) and the AED 100 is otherwise fully operable, the override period may extend to a month or more if no other fault is detected. Each of the override period extensions reduce further battery drain, allow for corrective action, to discourage detrimental battery removal, and to reduce the annoyances associated with unnecessary alarms.

AED 100 was previously described as comprising an optional wireless transceiver 106 which is in communicative connection with a remote device 124 and/or a remote service provider control station 160. FIG. 6 is a flowchart that illustrates one alternative embodiment of method 300 as shown by the flow path of branches "C" and "D". After a fault is detected at detecting step 306, method 300 automatically conducts a step 307 of transmitting an indication of the self-test failure alert via wireless transceiver 106. The transmission may be either to a remote device 124 or more preferably to a remote service provider control station 160. Responsive to the receipt of the alert at the RSP system 160 is an electronic acknowledgement transmission back to the wireless transceiver 106 which indicates that the information has been received. Upon the transceiver 106 receiving the acknowledgement, adjusting step 312 is triggered for adjusting the issuance of the self-test alarm to the third periodicity. Optionally, AED 100 may then indicate at step 380 an indication of the RSP acknowledgement so that local AED users understand that corrective action is underway. Method 300 then continues at resuming step 330 wherein after the predetermined correction period elapses, the second periodicity of the alarm issuance is resumed.

The RSP begins corrective action steps in parallel with the local method 300 steps. The RSP first initiates a corrective service action at step 332 which for example entails obtaining parts and arranging a service visit for the fault. Alternatively, the RSP can send corrective material, such as new batteries or electrodes, to the user for self-correction at sending step 334. Alternatively, the RSP can send a replacement device to the location for complete replacement. Finally, the RSP may dispatch a technician for local repair of the AED 100 at dispatching step 336.

After acknowledgment and receipt of self-test information at branch "C" and adjustment step, method 300 returns to a standby state of operation under the adjusted parameters. Monitoring of the AED 100 continues at step 308 as shown by branch "D". If no acknowledgment is every received by transceiver 106, then no adjustment to parameters occurs and the method directly returns to issuing step 308.

An alternative step of transmitting 340 to the RSP is shown in FIG. 3 as being responsive to the sensing step 310 instead of to the detecting step 306. Some users may prefer positive control of wireless communications, such that any transmission must be initiated only by a press of the override button first. Method steps as shown in FIG. 6 may then be conducted by the RSP 160 and processor 126 similarly to as described above.

The present invention is not intended to be restricted to the several embodiments of the invention described above. For example, the precise nature of the override input and the outputs may vary within the scope of the invention. Other variations that may be envisioned by those skilled in the art are intended to fall within the disclosure.

What is claimed is:

1. A method of maintaining a defibrillator, comprising the steps of:
    providing a defibrillator having a housing, a self-test circuit disposed within the housing and being configured to conduct an automatic self-test of the defibrillator on a first periodicity and being further configured to provide an initial determination output of a result of the self-test; a manual self-test override input disposed on an exterior surface of the housing; an audible output circuit in communication with the self-test circuit, the audible output operable to activate as an alarm repeating a plurality of times at a first periodicity in response to the result of the self-test; and a hardware processor in communication with the manual self-test override input and the self-test circuit, and configured to sense an activation of the manual self-test override input, wherein the hardware processor is configured to adjust the initial determination output to a subsequent determination output in response to a sensed activation of the manual self-test override input by the hardware processor, wherein the subsequent determination output comprises an audible output operating as an alarm repeating a plurality of times at a second periodicity for a predetermined correction period, the second periodicity being less than the first periodicity; wherein the hardware processor is further configured to revert to the initial determination output at the end of the predetermined correction period;
    conducting an automatic self-test of the defibrillator;
    detecting a self-test fault from the conducting step;
    issuing an alarm via the audible output responsive to the detecting step, the alarm repeating a plurality of times at a second periodicity;
    sensing an activation of the manual self-test override input subsequent to the issuing step;
    adjusting the issuing of the alarm to repeat a plurality of times at a third periodicity, that is less than the second periodicity, based on the sensing step; and
    resuming the issuing of the alarm a plurality of times at the second periodicity after a predetermined correction period.

2. The method of claim 1, further comprising the step of adjusting the first periodicity based on the sensing step.

3. The method of claim 2, further comprising the steps of:
    conducting a second automatic self-test subsequent to the adjusting step;
    detecting a correction of the self-test fault; and
    reverting to the first periodicity that was in effect prior to the sensing step.

4. The method of claim 1, wherein the providing step further comprises providing a wireless transceiver communicatively coupled to the hardware processor, and further comprising the step of transmitting a self-test fault alert via the wireless transceiver to a remote service provider responsive to the detecting step.

5. The method of claim 4, further comprising a step of receiving at the wireless transceiver an acknowledgement subsequent to the transmitting step, and further wherein the adjusting step and the resuming step are based on the receiving step.

6. The method of claim 4, wherein the remote service provider initiates a service action based on a receiving of the self-test fault alert.

7. The method of claim 6, wherein the service action comprises sending corrective material to the location of the defibrillator.

8. The method of claim 6, wherein the service action comprises sending a technician to the location of the defibrillator.

9. The method of claim 1, wherein the providing step further comprises providing a wireless transceiver communicatively coupled to the hardware processor, and further comprising a step of transmitting a self-test fault alert via the wireless transceiver to a remote service provider responsive to the sensing step.

10. The method of claim 1, further comprising a step of indicating at the audible output that the sensing step is completed.

11. A device, comprising:
    a defibrillator having a housing;
    a self-test circuit disposed within the housing and being configured to conduct an automatic self-test of the defibrillator on a first periodicity and being further configured to provide an initial determination output of a result of the self-test;
    a manual self-test override input disposed on an exterior surface of the housing;
    an audible output circuit in communication with the self-test circuit, the audible output operable to activate as an alarm repeating a plurality of times at a first periodicity in response to the result of the self-test; and
    a hardware processor in communication with the manual self-test override input and the self-test circuit, and configured to sense an activation of the manual self-test override input, wherein the hardware processor is configured to adjust the initial determination output to a subsequent determination output in response to a sensed activation of the manual self-test override input by the hardware processor, wherein the subsequent determination output comprises an audible output operating as an alarm repeating a plurality of times at a second periodicity for a predetermined correction period, the second periodicity being less than the first periodicity;
    wherein the hardware processor is further configured to revert to the initial determination output at the end of the predetermined correction period.

12. The defibrillator of claim 11, further comprising a wireless transceiver controllably coupled to the hardware processor, wherein the hardware processor and the wireless transceiver are configured to transmit a self-test fault alert responsive to the sensed operation of the manual self-test override input.

13. The defibrillator of claim 11, further comprising a wireless transceiver controllably coupled to the hardware processor, wherein the hardware processor and the wireless transceiver are configured to transmit a self-test fault alert responsive to an initial determination output of a failed self-test.

14. The defibrillator of claim 13, wherein the hardware processor is further configured to adjust the determination output in response to a sensed receipt of a manual override acknowledgement signal from the wireless transceiver to one of a deferral of the initial determination output and a reduction in a frequency of the initial determination output for a predetermined correction period.

15. The defibrillator of claim 13, wherein the hardware processor is further configured to adjust the first periodicity of the automatic self-test in response to a sensed receipt of a manual override signal from the wireless transceiver for a predetermined correction period.

16. A method of maintaining a defibrillator, comprising the steps of:
 providing a defibrillator having a housing with an exterior surface, a self-test circuit disposed within the housing and being configured to conduct an automatic self-test of the defibrillator on a first periodicity and being further configured to provide a determination output of a result of the self-test, a manual self-test override input disposed on the housing exterior, an audible output in communication with the self-test circuit to activate in response to the determination output, and a hardware processor in communication with the manual self-test override input and the self-test circuit, wherein the hardware processor is configured to adjust the determination output in response to a sensed operation of the manual self-test override input;
 conducting an automatic self-test of the defibrillator;
 detecting a self-test fault from the conducting step;
 issuing an alarm via the audible output responsive to the detecting step, the alarm repeating a plurality of times at a second periodicity;
 activating the manual self-test override input subsequent to the issuing step;
 sensing the activation of the manual self-test override input from the activating step;
 adjusting the issuing of the alarm to repeat a plurality of times at a third periodicity, that is less than the second periodicity, based on the sensing step; and
 resuming the issuing of the alarm a plurality of times at the second periodicity after a predetermined correction period.

* * * * *